United States Patent [19]

Honda et al.

[11] Patent Number: 5,198,579

[45] Date of Patent: Mar. 30, 1993

[54] CATALYST FOR OXIDIZING METHACROLEIN AND METHOD FOR PREPARING METHACRYLIC ACID

[75] Inventors: Tadatoshi Honda, Kanagawa; Nobuhiko Horiuchi; Jun Kitagawa, both of Yamaguchi; Masami Murakami, Kanagawa; Kazunori Kawahara, Yamaguchi; Hirofumi Io, Kanagawa, all of Japan

[73] Assignee: Mitsui Toatsu Chemicals, Inc., Tokyo, Japan

[21] Appl. No.: 789,926

[22] Filed: Nov. 12, 1991

[30] Foreign Application Priority Data

Nov. 14, 1990 [JP] Japan .................................. 2-306140
Jan. 28, 1991 [JP] Japan .................................. 3-008049

[51] Int. Cl.$^5$ ..................... C07C 51/16; C07C 51/235
[52] U.S. Cl. ..................................................... 562/535
[58] Field of Search ........................................ 562/535

[56] References Cited

U.S. PATENT DOCUMENTS 3,998,876 12/1976 Kato et al. ..................... 562/535

FOREIGN PATENT DOCUMENTS 0060066 9/1982 European Pat. Off. .
0350862 1/1990 European Pat. Off. .
0418657 3/1991 European Pat. Off. .
0442517 8/1991 European Pat. Off. .

*Primary Examiner*—José G. Dees
*Assistant Examiner*—Joseph M. Conrad
*Attorney, Agent, or Firm*—Oblon, Spivak, McClelland, Maier & Neustadt

[57] ABSTRACT

A composite oxide catalyst represented by the general formula: Mo-V-P-X-Y (wherein X represents at least one element selected from the group consisting of Sb, Cu, Co, Bi and As; Y represents at least one element selected from the group consisting of K, Rb, Cs and Tl) and a method for preparing methacrylic acid through gas phase catalytic oxidation of methacrolein with molecular oxygen in the presence of the foregoing catalyst are herein disclosed. The catalyst exhibits excellent catalytic activity, selectivity to methacrylic acid, catalytic stability and lifetime.

4 Claims, No Drawings

CATALYST FOR OXIDIZING METHACROLEIN AND METHOD FOR PREPARING METHACRYLIC ACID

BACKGROUND OF THE INVENTION (a) Field of the Invention

The present invention relates to a catalyst used in the preparation of methacrylic acid by gas phase catalytic oxidation of methacrolein with molecular oxygen and a method for preparing methacrylic acid which comprises catalytically oxidizing, in a gas phase, methacrolein with molecular oxygen in the presence of the catalyst.

(b) Description of the Prior Art

Up to now, there have been variously proposed catalysts used in preparing methacrylic acid through gas phase catalytic oxidation of methacrolein with molecular oxygen However, these catalysts are incomplete in properties such as catalytic activity, selectivity to methacrylic acid, stability and lifetime. Moreover, if they are prepared in an industrial scale, the quality thereof varies from lot to lot. Therefore, there has been desired to eliminate these drawbacks.

Composite oxide catalysts of Mo V-P-X-Y type (wherein X is at least one element selected from the group consisting of Sb, Cu, Co, Bi and As; and Y is at least one element selected from the group consisting of K, Rb, Cs and Tl), in particular Mo-V-P-Sb-Y type ones, i.e., those having the foregoing compositional formula in which X is Sb have widely been used, in this field, as catalysts for oxidizing methacrolein. In the conventional methods, these catalysts have in general been prepared by mixing aqueous solutions containing catalyst components and oxides, concentrating the mixture to dryness with heating and stirring and then calcining the concentrate. In addition, antimony trioxide has widely been used as a source of Sb as disclosed in, for instance, Japanese Unexamined Patent Publication (hereinafter referred to as "J. P. KOKAI") Nos. Sho 50-101316, Sho 52-68122, Sho 61-114739 and Sho 63 112535. However, it has been known, as disclosed in J.P. KOKAI No. Sho 61-114739, that the catalysts thus prepared by the conventional methods while using commercially available antimony trioxide as an Sb source do not always have satisfied catalytic activity, selectivity to methacrylic acid, stability and lifetime unless the starting antimony trioxide is pulverized into fine particles having an average particle size of not more than $0.2\mu$. However, such pulverization into an average particle size of not more than $0.2\mu$ is not practical.

In addition, there have widely been used, in this field, spherical or cylindrical catalysts, but recently there has been proposed the use of ring-like catalysts for preparing methacrylic acid at a high space velocity in high yield. However, such ring-like catalysts are liable to be broken into powder during packaging the catalysts and if they are packaged in a multi-tubular reactor of industrial-scale, the pressure difference in the reactor becomes large due to the pulverization of catalysts into powder and accordingly catalytic performances (activity and selectivity) which would be anticipated in the laboratory scale reaction cannot always be obtained.

In this field, the product (methacrylic acid) has been produced in an amount of several ten thousand tons-/year/production apparatus. Therefore, the improvement in yield by only several percentages can provide a significant economical effect. Thus, many attempts have been directed towards the improvement in the initial quality of a catalyst used therein and the development of methods for preparing high quality catalysts in good reproducibility.

SUMMARY OF THE INVENTION

Accordingly, an object of the present invention is to provide a composite oxide catalyst for preparing methacrylic acid through gas phase catalytic oxidation of methacrolein with molecular oxygen, which is excellent in catalytic activity, selectivity to methacrylic acid, stability and lifetime and more particularly to provide a composite oxide catalyst of a type represented by the following formula: Mo-V-P-X-Y (wherein X represents at least one element selected from the group consisting of Sb, Cu, Co, Bi and As; Y represents at least one element selected from the group consisting of K, Rb, Cs and Tl).

Another object of the present invention is to provide a means for preparing the foregoing catalyst in good reproducibility.

DETAILED DESCRIPTION OF THE INVENTION

The inventors of this invention have conducted intensive studies for the development of a composite oxide catalyst having a compositional formula: Mo-V-P-X-Y (wherein X represents at least one element selected from the group consisting of Sb, Cu, Co, Bi and As; Y represents at least one element selected from the group consisting of K, Rb, Cs and Tl) in particular a catalyst represented by the foregoing general formula in which X is Sb, i.e., Mo-V-P Sb-Y type composite oxide catalysts having excellent catalytic activity, selectivity to methacrylic acid, stability and lifetime For this purpose, the inventors have investigated the problems associated with the conventional preparation methods, in particular catalytic components, compositions thereof, shapes thereof and methodology for obtaining the same.

The inventors have considered that, in the conventional preparation methods, the resulting catalysts are not homogeneous since the foregoing component X, for instance, antimony trioxide is precipitated and dried without sufficiently dissolving it prior to the precipitation and have investigated a method which comprises completely dissolving antimony trioxide to give a homogeneous solution, then precipitating and drying. As a result, the inventors have found out a method for preparing a catalyst which can provide a catalyst having good quality in high reproducibility and which can provide a catalyst having various excellent properties such as activity, selectivity to methacrylic acid, stability of catalytic activity and lifetime and thus have completed the present invention.

According to a first aspect of the present invention, there is provided a catalyst used in preparing methacrylic acid through gas phase catalytic oxidation of methacrolein with molecular oxygen, which has a composition represented by the following general formula:

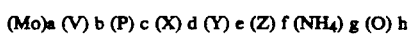

$(Mo)_a (V)_b (P)_c (X)_d (Y)_e (Z)_f (NH_4)_g (O)_h$ (wherein X represents at least one element selected from the group consisting of Sb, Cu, Co, Bi and As; Y represents at least one element selected from the group consisting of K, Rb, Cs and Tl; Z represents at least one element selected from the group consisting of W, Be, Mg, S, Ca, Sr, Ba, Te, Se, Ce, Ge, Mn, Zn, Cr, Ag, Pb, B, Nb, Cd, Sn, Al, Ti and Si; a to g each represents a relative ratio of each corresponding element and if a is assumed to be 12, b=0.1 to 2; c=1 to 3; d=0.01 to 3; e=0.1 to 3; f=0 to 2; and e+g=2 to 6; and h is the number of oxygen atoms required for satisfying the atomic valencies of the foregoing elements) and which is prepared by mixing a uniform solution containing Mo, V, P and X as compositional elements for the catalyst, a uniform solution containing Y as a compositional element for the catalyst, optionally a uniform solution containing Z as a compositional element for the catalyst and optionally ammonia and then drying the resulting product.

In the present invention, it is preferable to use compounds which can be decomposed in the form of oxides thereof in the course of the preparation of the catalyst as starting materials. Such compounds are, for instance, nitrates, salts with organic acids, hydroxides and oxides. Ammonium salts may likewise be used without any problem if they are added after uniformly dissolving an Sb source. Moreover, examples of silica sources usable in the invention include silica sol, silica gel, silicic acid esters and silicates.

In the present invention, oxides are used as sources of elements represented by X. For instance, antimony trioxide is used as an Sb source as in the conventional preparation methods because of easy availability thereof.

In the first aspect of the present invention, ammonium salts should not be used as sources of Mo, V and P. If ammonium salts are used as starting material, a uniform solution can be obtained in case of three component system, Mo-V-P, while it is difficult to uniformly dissolve antimony trioxide in case of four component system, Mo-V-P-X, in particular Mo-V-P-Sb and thus the resulting solution is subjected to the subsequent processes such as precipitation, concentration and drying without formation of a uniform solution containing Sb, so far as the inventors know. This leads to the formation of a catalyst having not only a scattered activity but also insufficient quality and stability due to uneven composition of the resulting catalyst However, in the conventional methods (for instance, those disclosed in J. P. KOKAI Nos. Sho 50-101316, Sho 52-68122, Sho 61-114739, Sho 61-283352 and Sho 63-112535), there are used ammonium paramolybdate as an Mo source and ammonium metavanadate as a V source because of high water-solubilities thereof as is described in J. P. KOKAI No. Sho 61-283352. For this reason, the conventional methods cannot provide high quality catalysts in good reproducibility.

In the first aspect of the present invention, a uniform solution containing Mo, V, P and X (wherein X represents at least one element selected from the group consisting of Sb, Cu, Co, Bi and As) is first prepared, then the solution is mixed with a uniform solution containing Y (wherein Y represents at least one element selected from the group consisting of K, Rb, Cs and Tl) and ammonia and the resulting product is dried. On the other hand, nitrates of, for instance, K, Rb, Cs and Tl are added prior to the addition of Sb in the conventional methods (see, for instance, J. P. KOKAI Nos. Sho 50-101316, Sho 61-114739 and Sho 63-112535). However, if compounds of K, Rb, Cs and Tl are added prior to the addition of Sb, they are precipitated through the formation of insoluble salts with Mo, V, P. This inhibits the dissolution of antimony trioxide subsequently added thereto and hence the resulting catalyst has non-uniform catalytic activity.

Solutions containing catalyst components used in the invention may be prepared by, for instance, the following manner. Molybdenum trioxide, vanadium pentoxide and oxides of elements X (for instance, antimony trioxide and copper oxide) are added to an aqueous solution of phosphoric acid and heated under reflux to dissolve these components. The resulting solution is referred to as a first starting solution. Aqueous ammonia is used as a second starting solution. Salts of at least one element selected from the group consisting Of K, Rb, Cs and Tl, for instance, nitrates are dissolved in pure water to give a third starting solution.

In the present invention, the catalyst may optionally comprise at least one element selected from the group consisting of W, Be, Mg, S, Ca, Sr, Ba, Te, Se, Ce, Ge, Mn, Zn, Cr, Ag, Pb, B, Nb, Cd, Sn, Al, Ti and Si. Compounds of these elements are added to either of the foregoing solutions so as to give a uniform solution or an independent solution containing the same is separately prepared.

In the present invention, at least two solutions containing these catalyst components are mixed and the resulting product is dried. The solutions may be mixed by the usual mixing means with stirring, but preferably by the use of a line mixer or a static mixer. The drying methods and conditions therefor are not restricted to those specific ones and those currently used in this field can be used in the present invention without any modification.

In the first aspect of the present invention, a uniform solution containing Mo, V, P and X is first prepared and then the solution is mixed with a uniform solution containing at least one element selected from the group consisting of K, Rb, Cs and Tl and ammonia. At this stage, the temperature of the solution or of the mixing process is reduced to preferably 0° to 25° C., more preferably 0° to 20° C. and most preferably 0° to 15° C. If, after the preparation of the uniform solution containing Mo, V, P and X, the uniform solution containing at least one element selected from the group consisting of K, Rb, Cs and Tl and ammonia are added thereto without controlling the temperature of the mixing process, any catalyst having constant quality is not obtained, in other words, good reproducibility in the catalyst quality is not achieved. If the temperature of the solution exceeds 30° C., the resulting heteropoly-acid salt has unstable structure and if it exceeds 40° C., a part of the resulting heteropoly-acid salt starts decomposition. Thus, the mixing temperature is preferably not more than 25° C., more preferably not more than 20° C. and most preferably 0° to 15° C. for ensuring the stable production of the heteropoly acid salt. Moreover, if the mixing temperature is increased to more than the upper limit, the resulting catalyst tends to cause an abrupt decrease in its activity.

According to the present invention, there is also provided a catalyst used in preparing methacrylic acid through gas phase catalytic oxidation of methacrolein with molecular oxygen, which has a composition represented by the following general formula:

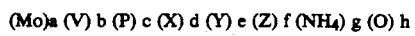

(wherein X represents at least one element selected from the group consisting of Sb, Cu, Co, Bi and As; Y represents at least one element selected from the group consisting of K, Rb, Cs and Tl; Z represents at least one element selected from the group consisting of W, Be, Mg, S, Ca, Sr, Ba, Te, Se, Ce, Ge, Mn, Zn, Cr, Ag, Pb, B, Nb, Cd, Sn, Al, Ti and Si; a to g each represents a relative ratio of each corresponding element and if a is assumed to be 12, b=0.1 to 2; c=1 to 3; d=0.01 to 3; e=0.1 to 3; f=0 to 2; and e+g=2 to 6; and h is the number of oxygen atoms required for satisfying the atomic valencies of the foregoing elements) and which is prepared by mixing a uniform solution containing Mo, V, P and X as compositional elements for the catalyst, a uniform solution containing Y as a compositional element for the catalyst, optionally a uniform solution containing Z as a compositional element for the catalyst and optionally ammonia at a temperature ranging from 0° to 25° C. and then drying the resulting product.

The reason why the quality of the resulting catalyst is impaired when it is prepared at a high mixing temperature has not yet clearly been elucidated, but it can be assumed that local high pH regions are formed during adding, to the uniform solution containing Mo, V, P and X, the uniform solution containing at least one element selected from the group consisting of K, Rb, Cs and Tl and ammonia, the heteropoly-acid formed comes in contact with these high pH regions, thus a part thereof is decomposed and this leads to the formation of undesirable catalyst structure. As the temperature increases, this tendency becomes more conspicuous.

The conventional methods do not specify the temperature during adding, to the uniform solution containing Mo, V, P and X, the uniform solution containing at least one element selected from the group consisting of K, Rb, Cs and Tl and ammonia and it has not conventionally been recognized that the quality of the resulting catalyst greatly varies depending on this temperature. For instance, in the example disclosed in J. P. KOKAI No. Sho 55-122734 which relates to a catalyst of Mo-V-P-As type, after adding cesium hydroxide to a heteropoly-acid prepared by heating for 3 hours with stirring, the resulting mixture is boiled under reflux for additional 3 hours and the solution is not cooled during the mixing procedure. Moreover, in the example disclosed in J. P. KOKAI No. Sho 59-4445, ammonia is added to a solution maintained at 80° C. together with other components.

If the catalyst has the foregoing composition, the final pH during mixing is desirably not more than 4. If the pH is controlled to a level of not more than 4, the structure of the resulting heteropoly-acid salt is firmly maintained and hence the quality of the resulting catalyst is not impaired at all, even if a low drying speed is adopted in the subsequent drying process. Therefore, the drying process can be performed in accordance with the method currently used in this field.

The dried catalyst powder is optionally calcined, molded and fired at a temperature ranging from 200° to 400° C. for 1 to 20 hours.

The catalyst of the present invention thus prepared has a crystalline structure similar to the heteropoly-acid salt formed.

The resulting catalyst having particulate or molded form can be used in the form of a fixed bed or may likewise be used in the form of a moving bed or a fluidized bed.

The inventors of this invention have also intensively investigated the shapes of the catalysts. As a result, it has been found out that if a spoke-ring shaped catalyst is used in the form of a fixed bed, the catalyst exhibits activity, selectivity to methacrylic acid and stability higher than those observed for the catalyst having a spherical and cylindical shapes although they are prepared or formed into these shapes using the same lot of starting catalyst powder. This clearly indicates that the shape of the catalyst is very important and critical for substantially improving properties thereof such as activity, selectivity to methacrylic acid and stability.

More specifically, the catalyst more preferably used should have a spoke-ring shape having an outer diameter ranging from 4 to 15 mm and a ring thickness ranging from 0.5 to 3 mm. In addition, the number of spokes is preferably not less than 2, but in general not more than 8. The thickness of the spoke ranges from 0.5 to 3 mm and the height thereof is selected so as to fall within the range of from 0.5 to 2 times the outer diameter of the ring. If the outer diameter of the catalyst is greater than 15 mm, the voidage thereof is very high and the activity thereof per unit space is lowered when it is packaged in a reactor tube usually employed having an inner diameter of the order of 200 mm. Moreover, if the thickness of the ring and spoke is less than 0.5 mm, the catalyst is extremely powdered during packaging the catalyst, while if it is more than 3 mm, effects of increasing the external surface area and of decreasing the pressure difference would not be anticipated.

Thus, according to a third aspect of the present invention, there is provided a catalyst used in preparing methacrylic acid through gas phase catalytic oxidation of methacrolein with molecular oxygen, which has a composition represented by the following general formula:

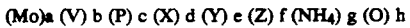

(Mo)a (V) b (P) c (X) d (Y) e (Z) f (NH4) g (O) h (wherein X represents at least One element selected from the group consisting of Sb, Cu, Co, Bi and As; Y represents at least one element selected from the group consisting of K, Rb, Cs and Tl; Z represents at least one element selected from the group consisting of W, Be, Mg, S, Ca, Sr, Ba, Te, Se, Ce, Ge, Mn, Zn, Cr, Ag, Pb, B, Nb, Cd, Sn, Al, Ti and Si; a to g each represents a relative ratio of each corresponding element and if a is assumed to be 12, b=0.1 to 2; c=1 to 3; d=0.01 to 3; e=0.1 to 3; f=0 to 2; and e+g=2 to 6; and h is the number of oxygen atoms required for satisfying the atomic valencies of the foregoing elements), which is prepared by mixing a uniform solution containing Mo, V, P and X as compositional elements for the catalyst, a uniform solution containing Y as a compositional element for the catalyst, optionally a uniform solution containing Z as a compositional element for the catalyst and optionally ammonia and then drying the resulting product and which is in the form of a spoke-ring shape having an outer diameter of 4 to 15 mm.

The catalyst according to the third aspect can be molded in the spoke-ring shape by any known method currently used in this field such as extrusion molding or tableting.

An optimum result can be obtained through the combination of the foregoing second and third aspects.

Thus, according to a fourth aspect of the present invention, there is provided a catalyst used in preparing methacrylic acid through gas phase catalytic oxidation of methacrolein with molecular oxygen, which has a composition represented by the following general formula:

$(Mo)_a (V)_b (P)_c (X)_d (Y)_e (Z)_f (NH_4)_g (O)_h$ (wherein X represents at least one element selected from the group consisting of Sb, Cu, Co, Bi and As; Y represents at least one element selected from the group consisting of K, Rb, Cs and Tl; Z represents at least one element selected from the group consisting of W, Be, Mg, S, Ca, Sr, Ba, Te, Se, Ce, Ge, Mn, Zn, Cr, Ag, Pb, B, Nb, Cd, Sn, Al, Ti and Si; a to g each represents a relative ratio of each corresponding element and if a is assumed to be 12, b=0.1 to 2; c=1 to 3; d=0.01 to 3; e=0.1 to 3; f=0 to 2; and e+g=2 to 6; and h is the number of oxygen atoms required for satisfying the atomic valencies of the foregoing elements), which is prepared by mixing a uniform solution containing Mo, V, P and X as compositional elements for the catalyst, a uniform solution containing Y as a compositional element for the catalyst, optionally a uniform solution containing Z as a compositional element for the catalyst and optionally ammonia at a temperature ranging from 0° to 25° C. and then drying the resulting product and which is in the form of a spoke-ring shape having an outer diameter of 4 to 15 mm.

If the catalyst has a spoke-ring shape, the activity, selectivity to methacrylic acid and stability thereof are higher than those observed for the catalysts having spherical and cylindical shapes although they are prepared or formed into these shapes using the same lot of starting catalyst powder. Therefore, unlike the third aspect, good results can be obtained if precipitates are formed from a mixed solution which contains Mo, V, P, X, Y and optionally Z and ammonia as compositional elements for the catalyst and in which the component X is not completely dissolved.

Thus, according to a fifth aspect of the present invention, there is provided a catalyst used in preparing methacrylic acid through gas phase catalytic oxidation of methacrolein with molecular oxygen, which has a composition represented by the following general formula:

$(Mo)_a (V)_b (P)_c (X)_d (Y)_e (Z)_f (NH_4)_g (O)_h$ (wherein X represents at least one element selected from the group consisting of Sb, Cu, Co, Bi and As; Y represents at least one element selected from the group consisting of K, Rb, Cs and Tl; Z represents at least one element selected from the group consisting of W, Be, Mg, S, Ca, Sr, Ba, Te, Se, Ce, Ge, Mn, Zn, Cr, Ag, Pb, B, Nb, Cd, Sn, Al, Ti and Si; a to g each represents a relative ratio of each corresponding element and if a is assumed to be 12, b=0.1 to 2; c=1 to 3; d=0.01 to 3; e=0.1 to 3; f=0 to 2; and e+g=2 to 6; and h is the number of oxygen atoms required for satisfying the atomic valencies of the foregoing elements); which is prepared by forming precipitates from a mixed solution which contains Mo, V, P, the foregoing component X, the foregoing component Y and optionally the component Z and ammonia as compositional elements for the catalyst and in which the component X is not completely dissolved in the mixed solution and then drying the resulting product; and which is in the form of a spoke-ring shape having an outer diameter of 4 to 15 mm.

The present invention also relates to a method for preparing methacrylic acid through gas phase catalytic oxidation of methacrolein with molecular oxygen in the presence of one of the foregoing catalysts.

In the gas phase catalytic oxidation reaction according to the present invention, the starting gas used comprises, for instance, 1 to 10% by volume of methacrolein, 3 to 20% by volume of molecular oxygen and 70 to 90% by volume of diluent gas. The starting gas mixture is fed to or passed through the foregoing catalyst at a temperature ranging from 250° to 450° C., a pressure of from ordinary pressure to 10 atm. and a space velocity ranging from 300 to 5,000/hr to perform the oxidation reaction. As the molecular oxygen, air is usually used, but pure oxygen gas may also be used. Examples of the diluent gases used include inert gases such as nitrogen and carbon dioxide. Alternatively, a part of the non-condensed gas included in the gaseous reaction mixture can be used as the diluent gas by recycling the same. Water vapor is preferably used together with the diluent gas to enhance the activity and selectivity of the catalyst. In such case, the amount of the water vapor to be incorporated into the starting gas mixture is usually up to 60% by volume.

The present invention will hereunder be described in more detail with reference to the following non-limitative working Examples and the effects practically achieved by the present invention will also be discussed in detail in comparison with Reference Examples given below. In the following Examples and Reference Examples, conversion and selectivity are defined as follows, respectively.

Conversion (%) =

$$\frac{\text{(molar number of reacted methacrolein)}}{\text{(molar number of methacrolein supplied)}} \times 100$$

Selectivity (%) =

$$\frac{\text{(molar number of methacrylic acid formed)}}{\text{(molar number of reacted methacrolein)}} \times 100$$

EXAMPLE 1

To 5800 ml of water, there were added 94 g of 85% phosphoric acid, 1000 g of molybdenum trioxide, 63 g of vanadium pentoxide and 19.2 g of copper oxide with heating under stirring, and the mixture was heated under reflux for 3 hours to give a uniform solution (Solution A). Commercially available antimony trioxide (33.8 g) was added to Solution A and the mixture was refluxed under heating for 3 hours to give a uniform solution which was used as a first starting solution. A mixture of 135 g of 28% aqueous ammonia and 700 ml of water was prepared and used as a second starting solution (Solution B). Cesium nitrate (62 g) was dissolved in 900 ml of water to give a third starting solution (Solution C).

To the first starting solution, there were dropwise added, in order, Solution B and Solution C while maintaining the temperature of the first solution at 15° C. and the resulting slurry was spray-dried. The dried powder was calcined, formed into a cylindrical shape having 5 mm each of diameter and height, followed by calcination at 350° C. for 10 hours in the air to give a composite oxide catalyst having a ratio: Mo/V/P-/Cu/Sb/Cs/NH₄ of 12/1.1/1.4/0.4/0.4/0.55/3.8.

The resulting catalyst (240 ml) was charged in a ¾ inch-steel steel reactor tube, a starting gas comprising 3% by volume of methacrolein, 9% by volume of oxygen, 20% by volume of water vapor and the balance of nitrogen gas (68% by volume) was reacted under standard conditions, i.e., a reactor bath temperature of 300° C., a space velocity of 1500/hr and a pressure at the outlet of the reactor of 0.2 kgf/cm$^2$ at gauge pressure to evaluate the initial quality of the catalyst.

After the evaluation of the initial quality of the catalyst, a staring gas mixture comprising 5% by volume of methacrolein, 13% by volume of oxygen, 25% by volume of water vapor and the balance of nitrogen gas (57% by volume) was reacted for 10 days under forced deterioration conditions, i.e., a reactor bath temperature of 350° C., a space velocity of 30000/hr and a pressure at the outlet of the reactor of 0.2 kgf/cm$^2$ at gauge pressure, then the reaction was further continued under the foregoing standard conditions to evaluate the stability of the catalyst. The results thus obtained are listed in the following Table 1.

EXAMPLES 2 TO 5

To confirm whether the catalyst quality has any scattering or not, a first starting solution and Solutions B and C having the same compositions used in Example 1 were prepared, a catalyst was prepared in the same manner used in Example 1 to evaluate the quality thereof. The results obtained are summarized in Table 1.

REFERENCE EXAMPLES 1 TO 5

Solutions A, B and C having the same compositions used in Example 1 were prepared The same procedures used in Example 1 were repeated to give a catalyst and to evaluate the quality of the resulting catalyst except that there were drop wise added, in order, Solution B and Solution C to Solution A, then 33.8 g of commercially available antimony trioxide was added thereto, followed by refluxing under heating for 3 hours and spray-drying. The results thus obtained are summarized in Table 1.

EXAMPLES 6 TO 8

Composite oxide catalysts each having an atomic ratio shown in Table 2 were prepared in the same manner used in Example 1 to evaluate the quality thereof. The results obtained are listed in Table 2.

REFERENCE EXAMPLES 6 TO 8

Composite oxide catalysts each having an atomic ratio as shown in Table 2 were prepared in the same manner used in Reference Example 1 to evaluate the quality thereof. The results obtained are listed in Table 2.

As seen from the results obtained in Examples 1 to 5 and Reference Examples 1 to 5, the scattering in the quality of the catalyst according to the present invention from lot to lot is smaller than those observed for the catalysts obtained in Reference Examples. Moreover, as seen from the comparison of Examples 1 to 5 with Reference Examples 1 to 5; the comparison of Example 6 with Reference Example 6; the comparison of Example 7 with Reference Example 7; and the comparison of Example 8 with Reference Example 8, the initial quality and that observed after forced deterioration of the catalysts of the present invention are superior to those for the comparative catalysts although they have the same catalyst compositions.

REFERENCE EXAMPLE 9

The same procedures used in Example 1 were repeated to give a catalyst except that 1362 g of ammonium molybdate was substituted for the molybdenum trioxide used in Example 1 and that 81 g of ammonium metavanadate was substituted for the vanadium pentoxide used in Example 1. However, antimony trioxide was not completely dissolved. For this reason, the catalyst was prepared without completely dissolving the antimony trioxide to evaluate the quality thereof. The catalyst initially had a conversion of 76.5% and a selectivity of 76.8% and it had a conversion of 74.2% and a selectivity of 74.0% after the forced deterioration.

EXAMPLE 9

To 68000 ml of water, there were added 940 g of 85% phosphoric acid, 10000 g of molybdenum trioxide, 630 of vanadium pentoxide and 268 g of selenium trioxide with heating under stirring, and the mixture was heated under reflux for 3 hours. Then 316 g of antimony trioxide was added to the mixture and refluxed under heating for additional 3 hours to give a uniform solution After allowing the solution to cool, an aqueous solution containing 1350 g of 28% aqueous ammonia and 620 g of cesium nitrate in 9000 ml of water was added to the solution while maintaining its temperature to 15° C. and the resulting slurry was spray dried. The dried powder was calcined, formed into a spoke-ring shape having 5 mm each of diameter and height, a number of spokes of 2 and thicknesses of the ring and the spoke of 1 mm followed by calcination at 350° C. for 10 hours in the air to give a composite oxide catalyst having a ratio: Mo/V/P/Sb/Se/Cs/NH, of 12/1.1/1.1/0.4/0.4/0.55/3.8.

The resulting catalyst (1400 ml) was charged in a ⅜ inch-steel reactor tube, a starting gas comprising 3% by volume of methacrolein, 9% by volume of oxygen, 20% by volume of water vapor and the balance of nitrogen gas (68% by volume) was reacted under standard condition, i.e., a reactor bath temperature of 300° C., a space velocity of 1000/hr and a pressure at the outlet of the reactor of 0.2 kgf/cm$^2$ at gauge pressure to evaluate the initial quality of the catalyst.

After the evaluation of the initial quality of the catalyst, a staring gas mixture comprising 5% by volume of methacrolein, 13% by volume of oxygen, 25% by volume of water vapor and the balance of nitrogen gas (57% by volume) was reacted for 10 days under forced deterioration conditions, i.e., a reactor bath temperature of 350° C., a space velocity of 30000/hr and a pressure at the outlet of the reactor of 0.2 kgf/cm$^2$ at gauge pressure, then the reaction was further continued under the foregoing standard conditions to evaluate the stability of the catalyst. The results thus obtained are listed in the following Table 3.

REFERENCE EXAMPLE 10 TO 12

To make clear the effect of catalyst shapes on the catalyst quality, cylindrical and ring-like catalysts were prepared from the same lot of the catalyst powder used in Example 9 and the quality thereof was evaluated in the same manner used in Example 9. The results obtained are listed in Table 3.

REFERENCE EXAMPLE 13

To make clear the effect of catalyst size of spoke-ring shaped catalysts on the catalyst quality, a spoke-ring shaped catalyst having an outer diameter of 20 mm was prepared from the same lot of the catalyst powder used in Example 9 and the quality thereof was evaluated in the same manner used in Example 9. The results obtained are listed in the following Table 3.

EXAMPLES 10 TO 13

Composite oxide catalysts each having an atomic ratio shown in Table 3 were prepared in the same manner used in Example 9. The quality of the resulting catalyst was evaluated in the same manner used in Example 9. The results obtained are listed in Table 2.

REFERENCE EXAMPLES 14 TO 17

To make clear the effect of catalyst shapes on the catalyst quality, cylindrical catalysts which had widely been used in this field were prepared from the same lot of the catalyst powder used in Examples 10 to 13 and the quality thereof was evaluated in the same manner used in Example 9. The results obtained are listed in Table 3.

As seen from the comparison of the results observed in Example 9 with those obtained in Reference Example 10, the spoke-ring shaped catalyst of the present invention exhibits the initial activity and selectivity to methacrylic acid higher than those for the cylindrical catalyst having the same outer diameter and these properties of the former observed after the forced deterioration were likewise substantially superior to those for the latter. As seen from the data obtained in Reference Example 12, if the outer diameter of a cylindrical catalyst is reduced, the activity thereof increases, but the selectivity is not improved at all. As seen from the comparison of the data obtained in Example 10 with those obtained in Reference Example 11, a part of the ring-like catalyst is powdered to thus increase the pressure difference and the selectivity attained by the ring-like catalyst is correspondingly lower than that for the spoke-ring shaped catalyst. In addition, as seen from the data obtained in Reference Example 13, if the size of the catalyst is excessively large, the starting gas mixture blows through the catalyst layer and accordingly the conversion is lowered. As seen from the comparison of the data obtained in Examples 10 to 13 with those obtained in Reference Examples 14 to 17, the spoke-ring shaped catalyst of the present invention exhibits the initial activity and selectivity to methacrylic acid higher than those for the cylindrical catalyst having the same composition and these properties of the former observed after the forced deterioration were likewise substantially superior to those for the latter.

REFERENCE EXAMPLES 18

In Examples 9 to 13 and Reference Examples 10 to 17, 1400 ml of the catalysts were packed in the reactor at a height of 3.5 m which were similar to the practical reactor to perform quality evaluation. In this Reference Example, to make clear the effect of the height of the packed catalyst on the results obtained, the quality of a catalyst obtained from the same lot used in Reference Example 12 was evaluated in the same manner used in Examples 1 to 8 and Reference Examples 1 to 9 wherein the amount of the catalyst used was 240 ml and its height was 0.6 m. The results thus obtained are summarized in Table 3.

As seen from the results thus obtained, if a cylindrical catalyst is used and the height of the packed catalyst is small, the catalyst sufficiently shows its quality, but the quality thereof is decreased as the height increases. This indicates that the optimum effect of the spoke-ring shaped catalyst can be anticipated when the height of the catalyst packed is increased to a practical level.

EXAMPLES 14 AND 15

First, second and third starting solutions were prepared in the same manner used in Example 1. Then the same procedures used in Example 1 were repeated to prepare a catalyst and to evaluate the quality thereof except that, to the first starting solution, there were dropwise added the second and third starting solutions while maintaining the temperature of the first solution at 5° or 20° C. The results thus obtained are listed in Table 4.

REFERENCE EXAMPLES 19 and 20

First, second and third starting solutions were prepared in the same manner used in Example 1. Then the same procedures used in Example 1 were repeated to prepare a catalyst and to evaluate the quality thereof except that there were dropwise added the second and third starting solutions to the first starting solution, while maintaining the temperature of the first solution at 30° or 40° C. The results thus obtained are listed in Table 4.

As seen from the data obtained in Reference Examples 19 and 20, if a high temperature is used during the addition of the uniform solution containing at least one element selected from the group consisting of K, Rb, Cs and Tl and ammonia, the quality, in particular selectivity of the resulting catalyst is greatly lowered.

Thus, according to the present invention, catalysts having excellent selectivity to methacrylic acid and stability can be obtained in good reproducibility.

TABLE 1

|  |  | Example No. |  |  |  |  | Reference Example No. |  |  |  |  |
|---|---|---|---|---|---|---|---|---|---|---|---|
|  |  | 1 | 2 | 3 | 4 | 5 | 1 | 2 | 3 | 4 | 5 |
| Catalyst | Mo | 12 | 12 | 12 | 12 | 12 | 12 | 12 | 12 | 12 | 12 |
| Composition, | V | 1.1 | 1.1 | 1.1 | 1.1 | 1.1 | 1.1 | 1.1 | 1.1 | 1.1 | 1.1 |
| atomic | P | 1.4 | 1.4 | 1.4 | 1.4 | 1.4 | 1.4 | 1.4 | 1.4 | 1.4 | 1.4 |
| ratio | Sb | 0.4 | 0.4 | 0.4 | 0.4 | 0.4 | 0.4 | 0.4 | 0.4 | 0.4 | 0.4 |
|  | Cs | 0.55 | 0.55 | 0.55 | 0.55 | 0.55 | 0.55 | 0.55 | 0.55 | 0.55 | 0.55 |
|  | Cu | 0.4 | 0.4 | 0.4 | 0.4 | 0.4 | 0.4 | 0.4 | 0.4 | 0.4 | 0.4 |
|  | $NH_4$ | 3.8 | 3.8 | 3.8 | 3.8 | 3.8 | 3.8 | 3.8 | 3.8 | 3.8 | 3.8 |
| Initial Quality | Conversion (%) | 83.5 | 83.2 | 83.7 | 83.4 | 83.3 | 82.4 | 76.8 | 78.9 | 81.9 | 80.1 |
|  | Selectivity (%) | 81.1 | 81.2 | 81.0 | 81.3 | 81.2 | 77.4 | 78.1 | 77.7 | 77.1 | 76.4 |
| After Forced Deterioration | Conversion (%) | 83.4 | 83.0 | 83.6 | 83.2 | 83.2 | 81.1 | 76.0 | 77.1 | 78.4 | 77.9 |
|  | Selectivity (%) | 81.2 | 81.3 | 81.5 | 81.6 | 81.4 | 76.3 | 76.1 | 75.3 | 75.9 | 75.0 |

TABLE 2

|  |  | Ex. 6 | Ref. Ex. 6 | Ex. 7 | Ref. Ex. 7 | Ex. 8 | Ref. Ex. 8 |
|---|---|---|---|---|---|---|---|
| Catalyst | Mo | 12 | 12 | 12 | 12 | 12 | 12 |
| Composition, | V | 1.2 | 1.2 | 1.2 | 1.2 | 1.5 | 1.5 |
| atomic | P | 1.5 | 1.5 | 1.1 | 1.1 | 1.5 | 1.5 |
| ratio | Sb | 0.3 | 0.3 | 0.5 | 0.5 | 0.5 | 0.5 |
|  | Y | K 1.0 | K 1.0 | Rb 0.8 | Rb 0.8 | Tl 0.5 | Tl 0.5 |
|  | Z | Se 0.5 | Se 0.5 | Ge 0.5 | Ge 0.5 | Cd 0.2 | Cd 0.2 |
|  | NH$_4$ | 3.8 | 3.8 | 3.0 | 3.0 | 2.6 | 2.6 |
| Initial Quality | Conversion (%) | 82.4 | 79.6 | 82.7 | 78.3 | 82.8 | 78.9 |
|  | Selectivity (%) | 80.9 | 78.8 | 80.8 | 79.0 | 80.7 | 79.6 |
| After Forced | Conversion (%) | 82.3 | 75.9 | 81.9 | 76.2 | 82.5 | 74.8 |
| Deterioration | Selectivity (%) | 80.7 | 76.4 | 80.8 | 74.4 | 80.3 | 76.1 |

TABLE 3

| | Catalyst Composition (atomic ratio of Element) | | | | | | | Catalyst Shape | Catalyst Size | | Initial Quality | | Quality After Forced Deterioration | |
|---|---|---|---|---|---|---|---|---|---|---|---|---|---|---|
| | | | | | | | | | Outer Diameter mm | Thickness mm | Conversion % | Selectivity % | Conversion % | Selectivity % |
| | Mo | V | P | X | Y | Z | NH$_4$ | | | | | | | |
| Ex. | 12 | 1.1 | 1.4 | Sb 0.4 | Cs 0.55 | Se 0.4 | 3.8 | 2 spokes | 5 | 1 | 85.0 | 80.1 | 84.7 | 79.5 |
| Ref. Ex. | | | | | | | | | | | | | | |
| 10 | 12 | 1.1 | 1.4 | Sb 0.4 | Cs 0.5 | Se 0.4 | 3.8 | cylinder | 5 | | 80.0 | 70.3 | 76.0 | 70.4 |
| 11 | 12 | 1.1 | 1.4 | Sb 0.4 | Cs 0.5 | Se 0.4 | 3.8 | ring | 5 | 1 | 82.6 | 73.2 | 79.6 | 71.5 |
| 12 | 12 | 1.1 | 1.4 | Sb 0.4 | Cs 0.5 | Se 0.4 | 3.8 | cylinder | 3 | | 81.1 | 71.5 | 80.0 | 70.3 |
| 13 | 12 | 1.1 | 1.4 | Sb 0.4 | Cs 0.5 | Se 0.4 | 3.8 | 2 spokes | 20 | 3 | 80.7 | 75.1 | 80.2 | 71.4 |
| Ex. | | | | | | | | | | | | | | |
| 10 | 12 | 1.1 | 1.5 | Cu 0.2 | K 1.0 | Te 0.2 | 3.0 | 2 spokes | 5 | 1 | 86.1 | 82.0 | 85.4 | 81.2 |
| 11 | 12 | 1.2 | 1.1 | Bi 0.1 | Cs 2.0 | Nb 0.5 | 2.5 | 2 spokes | 5 | 1 | 84.4 | 81.7 | 84.2 | 80.0 |
| 12 | 12 | 1.2 | 1.5 | As 0.5 | Rb 1.5 | Ca 0.5 | 2.5 | 2 spokes | 5 | 1 | 83.6 | 80.6 | 83.3 | 80.1 |
| 13 | 12 | 1.5 | 1.8 | Co 1.0 | Tl 1.0 | Al 1.0 | 3.0 | 2 spokes | 5 | 1 | 85.7 | 80.9 | 85.1 | 81.3 |
| Ref. Ex. | | | | | | | | | | | | | | |
| 14 | 12 | 1.1 | 1.5 | Cu 0.2 | K 1.0 | Te 0.2 | 3.0 | cylinder | 3 | | 81.4 | 74.6 | 79.1 | 74.9 |
| 15 | 12 | 1.2 | 1.1 | Bi 0.1 | Cs 2.0 | Nb 0.5 | 2.5 | cylinder | 3 | | 82.3 | 72.3 | 80.3 | 71.7 |
| 16 | 12 | 1.2 | 1.5 | As 0.5 | Rb 1.5 | Ca 0.5 | 2.5 | cylinder | 3 | | 80.4 | 73.4 | 78.4 | 72.8 |
| 17 | 12 | 1.5 | 1.8 | Co 1.0 | Tl 1.0 | Al 1.0 | 3.0 | cylinder | 5 | | 81.7 | 71.9 | 79.4 | 71.3 |
| 18 | 12 | 1.1 | 1.4 | Sb 0.4 | Cs 0.5 | Se 0.4 | 3.8 | cylinder | 3 | | 81.6 | 80.3 | 81.3 | 80.0 |

Note:
In the column of Catalyst Shape, "2 spokes" means a spoke-ring shape having 2 spokes.
As to the catalyst size, the height of the catalyst particle is identical to the outer diameter.

TABLE 4

|  |  | Ex. 14 | Ex. 15 | Ref. Ex. 19 | Ref. Ex. 20 |
|---|---|---|---|---|---|
| Catalyst | Mo | 12 | 12 | 12 | 12 |
| Composition, | V | 1.1 | 1.1 | 1.1 | 1.1 |
| atomic | P | 1.4 | 1.4 | 1.4 | 1.4 |
| ratio | Sb | 0.4 | 0.4 | 0.4 | 0.4 |
|  | Cs | 0.55 | 0.55 | 0.55 | 0.55 |
|  | Cu | 0.4 | 0.4 | 0.4 | 0.4 |
|  | NH$_4$ | 3.8 | 3.8 | 3.8 | 3.8 |
| Solution Temperature (°C.) |  | 5 | 20 | 30 | 40 |
| Initial Quality | Conversion (%) | 82.2 | 82.6 | 78.4 | 71.1 |
|  | Selectivity (%) | 81.8 | 80.9 | 68.2 | 35.3 |
| After Forced | Conversion (%) | 83.3 | 82.4 | 76.9 | 65.8 |
| Deterioration | Selectivity (%) | 80.8 | 80.8 | 66.5 | 31.7 |

What is claimed is:

1. A method for preparing methacrylic acid comprising catalytically oxidizing, in a gas phase, methacrolein with molecular oxygen in the presence of a catalyst, said catalyst having a composition represented by the following formula:

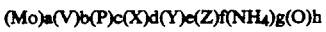

(Mo)$_a$(V)$_b$(P)$_c$(X)$_d$(Y)$_e$(Z)$_f$(NH$_4$)$_g$(O)$_h$ wherein x represents at least one element selected from the group consisting of Sb, Cu, Co, Bi and As; Y represents at least one element selected from the group consisting of K, Rb, Cs and Tl; Z represents at least one element selected from the group consisting of W, Be, Mg, S, Ca, Sr, Ba, Te, Se, Ce, Ge, Mn, Zn, Cr, Ag, Pb, B, Nb, Cd, Sn, Al, Ti and Si; a to g each represents a relative ratio of each corresponding element wherein if a is assumed to be 12, b=0.1 to 2; c=1 to 3; d=0.01 to 3; e=0.1 to 3; f=0 to 2; and e+g=2 to 6; h is the number of oxygen atoms required to satisfy the atomic valency of the foregoing elements and which is prepared by mixing a uniform solution containing Mo, V, P and X as compositional elements for the catalyst, a uniform solution containing Y as a compositional element for the catalyst, optionally a uniform solution containing Z as a compositional element for the catalyst and optionally ammonia at a temperature ranging from 0° to 25° C. and then drying the resulting product.

2. A method for preparing methacrylic acid comprising catalytically oxidizing, in a gas phase, methacrolein with molecular oxygen in the presence of a catalyst, said catalyst having a composition represented by the following formula:

$(Mo)_a(V)_b(P)_c(X)_d(Y)_e(Z)_f(NH_4)_g(O)_h$ (wherein X represents at least one element selected from the group consisting of Sb, Cu, Co, Bi and As; Y represents at least one element selected from the group consisting of K, Rb, Cs and Tl; Z represents at least one element selected from the group consisting of W, Be, Mg, S, Ca, Sr, Ba, Te, Se, Ce, Ge, Mn, Zn, Cr, Ag, Pb, B, Nb, Cd, Sn, Al, Ti and Si; a to g each represents a relative ratio of each corresponding element wherein if a is assumed to be 12, $b=0.1$ to 2; $c=1$ to 3; $d=0.01$ to 3; $e=0.1$ to 3; $f=0$ to 2; and $e+g=2$ to 6; h is the number of oxygen atoms required to satisfy the atomic valency of the foregoing elements and which is prepared by mixing a uniform solution containing Mo, V, P and X as compositional elements for the catalyst, a uniform solution containing y as a compositional element for the catalyst, optionally a uniform solution containing Z as a compositional element for the catalyst and optionally ammonia and then drying the resulting product and which is in the form of a spoke-ring shape having an outer diameter of 4 to 15 mm.

3. A method for preparing methacrylic acid comprising catalytically oxidizing, in a gas phase, methacrolein with molecular oxygen in the presence of a catalyst, said catalyst having a composition represented by the following formula:

$(Mo)_a(V)_b(P)_c(X)_d(Y)_e(Z)_f(NH_4)_g(O)_h$ wherein X represents at least one element selected from the group consisting of Sb, Cu, Co, Bi and As; Y represents at least one element selected from the group consisting of K, Rb, Cs and Tl; Z represents at last one element selected from the group consisting of W, Be, Mg, S, Ca, Sr, Ba, Te, Be, Ce, Ge, Mn, Zn, Cr, Ag, Pb, B, Nb, Cd, Sn, Al, Ti and Si; a to g each represents a relative ratio of each corresponding element wherein if a is assumed to be 12, $b=0.1$ to 2; $c=1$ to 3; $d=0.01$ to 3; $e=0.1$ to 3; $f=0$ to 2; and $e+g=2$ to 6; h is the number of oxygen atoms required to satisfy the atomic valency of the foregoing element s and which is prepared by mixing a uniform solution containing Mo, V, P and X as compositional element s for the catalyst, a uniform solution containing Y as a compositional element for the catalyst, optionally a uniform solution containing Z as a compositional element for the catalyst and optionally ammonia at a temperature ranging from 0° to 25° C. and then drying the resulting product and which is in the form of a spoke-ring shape having an outer diameter of 4 to 15 mm.

4. A method for preparing methacrylic acid comprising catalytically oxidizing, in a gas phase, methacrolein with molecular oxygen in the presence of a catalyst, said catalyst having a composition represented by the following formula:

$(Mo)_a(V)_b(P)_c(X)_d(Y)_e(Z)_f(NH_4)_g(O)_h$ (wherein X represents at least one element selected from the group consisting of Sb, Cu, Co, Bi and As; Y represents at least one element selected from the group consisting of K, Rb, Cs and Tl; Z represents at least one element selected from the group consisting of W, Be, Mg, S, Ca, Sr, Ba, Te, Se, Ce, Ge, Mn, Zn, Cr, Ag, Pb, B, Nb, Cd, Sn, Al, Ti and Si; a to g each represents a relative ratio of each corresponding element wherein if a is assumed to be 12, $b=0.1$ to 2; $c=1$ to 3; $d=0.01$ to 3; $e=0.1$ to 3; $f=0$ to 2; and $e+g=2$ to 6; h is the number of oxygen atoms required to satisfy the atomic valency of the foregoing elements and which is prepared by forming precipitates from a mixed solution which contains Mo, V, P, the foregoing component X, the foregoing Y as compositional elements for the catalyst, and optionally the component Z and ammonia as compositional elements for the catalyst and in which the component X is not completely dissolved in the mixed solution and then drying the resulting product; and which is the form of a spoke-ring shape having an outer diameter of 4 to 15 mm.

* * * * *